US011730368B1

(12) United States Patent
Lee et al.

(10) Patent No.: US 11,730,368 B1
(45) Date of Patent: Aug. 22, 2023

(54) APPARATUS AND METHOD FOR PROVIDING ALZHEIMER'S DIAGNOSIS ASSISTANCE INFORMATION USING MRI AND PET IMAGING

(71) Applicant: NEUROPHET Inc., Seoul (KR)

(72) Inventors: Ji Yeon Lee, Seoul (KR); Dong Hyeon Kim, Namyangju-si (KR); Min Ho Lee, Seoul (KR); Eun Young Kim, Gwacheon-si (KR)

(73) Assignee: NEUROPHET Inc., Seoul (KR)

( * ) Notice: Subject to any disclaimer, the term of this patent is extended or adjusted under 35 U.S.C. 154(b) by 0 days.

(21) Appl. No.: 18/054,072

(22) Filed: Nov. 9, 2022

(30) Foreign Application Priority Data

Feb. 22, 2022 (KR) .................... 10-2022-0023103

(51) Int. Cl.
| | | |
|---|---|---|
| *A61B 5/00* | (2006.01) | |
| *A61B 5/055* | (2006.01) | |
| *G16H 10/60* | (2018.01) | |
| *G16H 50/20* | (2018.01) | |
| *G16H 50/30* | (2018.01) | |

(52) U.S. Cl.
CPC ............ *A61B 5/0035* (2013.01); *A61B 5/055* (2013.01); *A61B 5/4088* (2013.01); *A61B 5/7264* (2013.01); *A61B 5/743* (2013.01); *G16H 10/60* (2018.01); *G16H 50/20* (2018.01); *G16H 50/30* (2018.01)

(58) Field of Classification Search
None
See application file for complete search history.

(56) References Cited

U.S. PATENT DOCUMENTS

2012/0323108 A1* 12/2012 Carroll .................. G06T 7/0012
                                                    600/407
2018/0204327 A1*  7/2018 Matthews ............ A61B 5/4064

OTHER PUBLICATIONS

Vemuri P, Lowe VJ, Knopman DS, Senjem ML, Kemp BJ, Schwarz CG, Przybelski SA, Machulda MM, Petersen RC, Jack CR Jr. Tau-PET uptake: Regional variation in average SUVR and impact of amyloid deposition. Alzheimers Dement (Amst). Dec. 21;6:21-30. (Year: 2016).*

(Continued)

*Primary Examiner* — Shahdeep Mohammed
*Assistant Examiner* — Amal Aly Farag
(74) *Attorney, Agent, or Firm* — Broadview IP Law, PC (57) ABSTRACT

Preferred embodiments of the present invention provide an apparatus and method for providing dementia diagnosis assistance information. In the present invention, an MRI brain image and a PET brain image of a subject for diagnosis are received, the MRI brain image is divided into a plurality of regions and registered with the PET brain image. Then, a standardized uptake value ratio (SUVR) of each divided region is obtained from the registered image, and for each divided region, a standard value indicating the degree of proximity of a SUVR of the subject to the average value of the SUVR of Alzheimer's group and the average value of the SUVR of the normal group is obtained. Then, the standard value of the SUVR of the subject is displayed together with the average value and the range of the standard deviation of each control group for each of the divided regions as a graph.

6 Claims, 8 Drawing Sheets

(56) References Cited

OTHER PUBLICATIONS

Kim, Seonjik et al. "Region of Interest Analysis for Standardized Uptake Value Ratio of F-fludeoxyglucose PET: Mild Cognitive Impairment and Alzheimer's Disease." Journal. Department of Biomedical Engineering, Daegu Catholic University. Nov. 5, 2018.
Extended European Search Report for EP22206524 by European Patent Office dated Feb. 10, 2023.
Yamao Tensho et al: "Centiloid scale analysis for 18F-THK5351 PET imaging in Alzheimer's disease", Physica Medica, ACTA Medica Edizioni E Congressi, Rome, IT, vol. 82, Feb. 1, 2021.
Row Christopher C et al: "18F-Florbetaben PET beta-amyloid binding expressed in Centiloids", European Journal of Nuclear Medicine and Molecular Imaging, Springer Berlin Heidelberg, Berlin/Heidelberg, vol. 44, No. 12, Jun. 22, 2017.

* cited by examiner

| ALZHEIMER'S GROUP | | | | | NORMAL GROUP | | | | |
|---|---|---|---|---|---|---|---|---|---|
| | $R_1$ | $R_2$ | $\cdots$ | $R_N$ | | $R_1$ | $R_2$ | $\cdots$ | $R_N$ |
| $A_1$ | $V_{A1R1}$ | $V_{A1R2}$ | | $V_{A1RN}$ | $B_1$ | $V_{B1R1}$ | $V_{B1R2}$ | | $V_{B1RN}$ |
| $A_2$ | $V_{A2R1}$ | $V_{A2R2}$ | | $V_{A2RN}$ | $B_2$ | $V_{B2R1}$ | $V_{B2R2}$ | | $V_{B2RN}$ |
| . | . | . | | . | . | . | . | | . |
| . | . | . | | . | . | . | . | | . |
| $A_M$ | $V_{AMR1}$ | $V_{AMR2}$ | | $V_{AMRN}$ | $B_M$ | $V_{BMR1}$ | $V_{BMR2}$ | | $V_{BMRN}$ |
| AVERAGE | $AV_{AR1}$ | $AV_{AR2}$ | | $AV_{ARN}$ | AVERAGE | $AV_{BR1}$ | $AV_{BR2}$ | | $AV_{BRN}$ |
| STANDARD DEVIATION | $\sigma_{AR1}$ | $\sigma_{AR2}$ | | $\sigma_{ARN}$ | STANDARD DEVIATION | $\sigma_{BR1}$ | $\sigma_{BR2}$ | | $\sigma_{BRN}$ |
| MILD COGNITIVE IMPAIRMENT GROUP | | | | | NORMAL AGING GROUP | | | | |
| | $R_1$ | $R_2$ | $\cdots$ | $R_N$ | | $R_1$ | $R_2$ | $\cdots$ | $R_N$ |
| $C_1$ | $V_{C1R1}$ | $V_{C1R2}$ | | $V_{C1RN}$ | $D_1$ | $V_{D1R1}$ | $V_{D1R2}$ | | $V_{D1RN}$ |
| $C_2$ | $V_{C2R1}$ | $V_{C2R2}$ | | $V_{C2RN}$ | $D_2$ | $V_{D2R1}$ | $V_{D2R2}$ | | $V_{D2RN}$ |
| . | . | . | | . | . | . | . | | . |
| . | . | . | | . | . | . | . | | . |
| $C_M$ | $V_{CMR1}$ | $V_{CMR2}$ | | $V_{CMRN}$ | $D_M$ | $V_{DMR1}$ | $V_{DMR2}$ | | $V_{DMRN}$ |
| AVERAGE | $AV_{CR1}$ | $AV_{CR2}$ | | $AV_{CRN}$ | AVERAGE | $AV_{DR1}$ | $AV_{DR2}$ | | $AV_{DRN}$ |
| STANDARD DEVIATION | $\sigma_{CR1}$ | $\sigma_{CR2}$ | | $\sigma_{CRN}$ | STANDARD DEVIATION | $\sigma_{DR1}$ | $\sigma_{DR2}$ | | $\sigma_{DRN}$ |

APPARATUS AND METHOD FOR PROVIDING ALZHEIMER'S DIAGNOSIS ASSISTANCE INFORMATION USING MRI AND PET IMAGING

CROSS-REFERENCE TO RELATED APPLICATIONS

This U.S. non-provisional patent application claims priority under 35 U.S.C. § 119 of Korean Patent Application No. 10-2022-0023103, filed on Feb. 22, 2022, the entire contents of which are hereby incorporated by reference.

FIELD OF THE INVENTION

The present invention disclosed herein relates to an apparatus and method for providing dementia diagnosis assistance information, and more particularly, to an apparatus and method for providing dementia diagnosis assistance information by acquiring a standardized uptake value ratio for a brain image of a subject for diagnosis.

BACKGROUND ART

Dementia refers to a clinical syndrome in which the cognitive functions of various regions, such as memory, language, and judgment, are reduced and daily life is unable to be properly performed. A typical dementia is senile dementia called Alzheimer's disease, and vascular dementia caused by stroke, and in addition, there is dementia due to various causes, but 50% to 70% of dementia patients are dementia due to Alzheimer's disease.

Alzheimer's disease develops long before symptoms appear, but changes in the brain are not easily noticed until symptoms appear. The time when conspicuous symptoms such as memory loss and language disorder appear is after some degree of brain change has already occurred. The symptoms are due to damage or destruction of nerve cells in the brain involved in thinking, learning, and memory (cognitive function). As the disease progresses, other neurons in the brain are damaged and destroyed, eventually affecting basic physical activities such as walking and swallowing food. Therefore, prompt and accurate diagnosis of Alzheimer's disease is very important.

As a method for diagnosing Alzheimer's disease and the resulting Alzheimer's dementia, there is a diagnostic method by an amyloid positron emission tomography (PET) image. The PET stands for a positron emission tomography and is method of photographing the inside of the body by injecting a test drug that emits radiation to a patient and detecting the radiation emitted by the drug from the outside. As the test drug, only amyloid beta may be labeled by administering the compound that is easily attached to amyloid beta. As a result, it is possible to check how much amyloid beta is accumulated in which part of the brain by using the image and analyze the accumulated area and amount for use to differentiate Alzheimer's disease patients.

A typical diagnostic method using amyloid PET is a method using amyloid standardized uptake value ratio (SUVR). Amyloid standardized uptake value ratio (SUVR) represents a ratio of amyloid standardized uptake value (SUV) from two different regions (target and reference region) within the same amyloid PET image, and the amyloid standardized uptake value (SUV) may represent the ratio of the concentration of radioactivity of the image to the concentration of radioactivity of the whole injected body.

The amyloid standardized uptake value ratio (SUVR) is being used as the main data for determining the progression of Alzheimer's disease. For example, the Alzheimer's Disease Neuroimaging Initiative (ADNI), an organization that collects data such as PET images and cognitive tests and conducts research by validating and utilizing the data, suggests an SUVR value of approximately 1.10 based on a florbetapir tracer, as a criterion for quantitatively classifying beta amyloid positive and negative. In this case, the value of 1.10 represents the confidence limit value for the top 5% of the distribution of the amyloid standardized uptake value ratio (SUVR) obtained from a control group of 21 people under the age of 55 years. That is, the ADNI suggests determining whether amyloid is positive or negative based on 1.10 of the amyloid standardized uptake value ratio (SUVR) through the analysis of amyloid PET images.

However, as a diagnosis result using amyloid PET images in the related art, only determination may be made as to whether amyloid is positive or negative, and there is a limitation in not providing additional information for determining whether dementia is positive or negative. In addition, when the standardized uptake value ratio is distributed around a threshold value of the amyloid positive or negative determination, there is a limitation in not providing more useful information to doctors who diagnose dementia.

SUMMARY OF THE INVENTION

In order to solve the problem described above, the present invention provides an apparatus and method for providing dementia diagnosis assistance information that provides various assistance information needed for dementia diagnosis to medical staff performing dementia diagnosis by using a PET images, in addition to simply providing a standardized uptake value ratio (SUVR), by generating a standard value indicating the degree to which the standardized uptake value ratio (SUVR) of the subject for diagnosis is close to the average value of SUVR of the normal group and the average value of SUVR of the Alzheimer's group and displaying the standard value as a graph of comparison with a control group.

In accordance with a preferred embodiment of the present invention in order to solve the aforementioned problems, disclosed is a method for providing dementia diagnosis assistance information that is performed in an apparatus for providing dementia diagnosis assistance information, the apparatus including a processor and a memory for storing predetermined instructions, the method including: (a) calculating a standardized uptake value ratio (SUVR) for each of regions (divided regions) obtained by dividing a brain region of a brain image of a subject for diagnosis into a plurality of predefined regions; (b) obtaining a standard value by mapping the standardized uptake value ratio of each divided region to a standard interval defined in advance for each divided region; and (c) outputting the standard value of each divided region together with statistical information about an average standard value of a control group for each divided region.

Further, in accordance with another embodiment of the present invention, the step (a) may include (a1) dividing the brain region included in a magnetic resonance imaging (MRI) image of the subject for diagnosis into a plurality of predefined divided regions and registering the image of the brain region with a positron emission tomography (PET) image of the subject for diagnosis, and (a2) generating a standardized uptake value ratio (SUVR) for each of the divided regions in the registered image.

Further, in accordance with another embodiment of the present invention, the standard value may represent a degree of proximity of the standardized uptake value ratio to an average value of standardized uptake value ratios of a group of Alzheimer's patients and an average value of standardized uptake value ratios of a normal group.

Further, in accordance with another embodiment of the present invention, the standard interval may be defined by setting, as both ends of a regular interval, the average value of the standardized uptake value ratios of the group of the Alzheimer's patients and the average value of the standardized uptake value ratios of the normal group for a region corresponding to each of the plurality of divided regions.

Further, in accordance with another embodiment of the present invention, the standard interval may be an interval generated by transforming the average value of the standardized uptake value ratios of the normal group to correspond to 0 according to a transformation formula, and transforming the average value of the standardized uptake value ratios of the group of the Alzheimer's patients to correspond to a predetermined number greater than 0 according to a predetermined transformation formula, and the standard value may be obtained by transforming the standardized uptake value ratio according to the transformation formula.

Further, in accordance with another embodiment of the present invention, the transformation formula may be defined as $$y = \frac{(x-B)}{(A-B)} \times 100,$$

where A represents the average value of the standardized uptake value ratios of the group of the Alzheimer's patients, B represents the average value of the standardized uptake value ratios of the normal group, and x represents a parameter to be transformed.

Further, in accordance with another embodiment of the present invention, the step (c) may include outputting a pair of values as large as a predefined value and small as a predefined value from the average standard value of the control group together with the standard value as a graph, for each divided region.

Further, in accordance with another embodiment of the present invention, the step (c) may include outputting a pair of values that differ by a standard deviation from the average standard value of the control group together with the standard value, for each divided region.

Further, in accordance with another embodiment of the present invention, the control group may include at least one of an Alzheimer's patient group, a mild cognitive impairment group, a normal aging group, and a normal group.

Further, in accordance with another embodiment of the present invention, the step (c) may include displaying a proportion of divided regions where the standard value is located between a pair of values of the control group or a proportion of divided regions where the standard value deviates from the pair of values of the control group together with the graph.

Further, in accordance with another embodiment of the present invention, the step (c) may include estimating that the subject for diagnosis belongs to the control group when the proportion of divided regions where the standard value is located between the pair of values of the control group is equal to or greater than a predefined threshold value, and outputting an estimation result together with the graph.

Further, in accordance with another embodiment of the present invention, the step (c) may include outputting a degree of agreement between a graph obtained by connecting the standard values and a graph obtained by connecting the average standard values of the control group together with the graph, for the divided regions.

In accordance with a preferred embodiment of the present invention in order to solve the aforementioned problems, disclosed is a computer program that is stored in a non-transitory storage medium and executed in a computer including a processor, the computer program performing the method for providing dementia diagnosis assistance information.

In accordance with a preferred embodiment of the present invention in order to solve the aforementioned problems, disclosed is an apparatus for providing dementia diagnosis assistance information, the apparatus including: a processor; and a memory for storing predetermined instructions, in which the processor is configured to, when executing the instructions stored in the memory: (a) calculate a standardized uptake value ratio (SUVR) for each of regions (divided regions) obtained by dividing a brain region of a brain image of a subject for diagnosis into a plurality of predefined regions; (b) obtain a standard value by mapping the standardized uptake value ratio of each divided region to a standard interval defined in advance for each divided region; and (c) output the standard value of each divided region together with statistical information about an average standard value of a control group for each divided region.

Further, in the apparatus in accordance with another embodiment of the present invention, in the step (a), the processor is further configured to: (a1) divide the brain region included in a magnetic resonance imaging (MRI) image of the subject for diagnosis into a plurality of predefined divided regions and register the image of the brain region with a positron emission tomography (PET) image of the subject for diagnosis; and (a2) generate a standardized uptake value ratio (SUVR) for each of the divided regions in the registered image.

Further, in the apparatus in accordance with another embodiment of the present invention, the standard value may represent a degree of proximity of the standardized uptake value ratio to an average value of standardized uptake value ratios of a group of Alzheimer's patients and an average value of standardized uptake value ratios of a normal group.

Further, in the apparatus in accordance with another embodiment of the present invention, the standard interval may be defined by setting, as both ends of a regular interval, the average value of the standardized uptake value ratios of the group of the Alzheimer's patients and the average value of the standardized uptake value ratios of the normal group for a region corresponding to each of the plurality of divided regions.

Further, in the apparatus in accordance with another embodiment of the present invention, the standard interval may be an interval generated by transforming the average value of the standardized uptake value ratios of the normal group to correspond to 0 according to a predetermined transformation formula, and transforming the average value of the standardized uptake value ratios of the group of the Alzheimer's patients to correspond to a predetermined number greater than 0 according to the transformation formula, and the standard value may be obtained by transforming the standardized uptake value ratio according to the transformation formula.

Further, in the apparatus in accordance with another embodiment of the present invention, the transformation formula may be defined as $$y = \frac{(x-B)}{(A-B)} \times 100,$$

where A represents the average value of the standardized uptake value ratios of the group of the Alzheimer's patients, B represents the average value of the standardized uptake value ratios of the normal group, and x represents a parameter to be transformed.

Further, in the apparatus in accordance with another embodiment of the present invention, in the step (c), the processor is further configured to output a pair of values as large as a predefined value and small as a predefined value from the average standard value of the control group together with the standard value as a graph, for each divided region.

Further, in the apparatus in accordance with another embodiment of the present invention, in the step (c), the processor is further configured to output a pair of values that differ by a standard deviation from the average standard value of the control group together with the standard value, for each divided region.

Further, in the apparatus in accordance with another embodiment of the present invention, the control group may include at least one of an Alzheimer's patient group, a mild cognitive impairment group, a normal aging group, and a normal group.

Further, in the apparatus in accordance with another embodiment of the present invention, in the step (c), the processor is further configured to display a proportion of divided regions where the standard value is located between a pair of values of the control group or a proportion of divided regions where the standard value deviates from the pair of values of the control group together with the graph.

Further, in the apparatus in accordance with another embodiment of the present invention, in the step (c), the processor is further configured to estimate that the subject for diagnosis belongs to the control group when the proportion of divided regions where the standard value is located between the pair of values of the control group is equal to or greater than a predefined threshold value, and output an estimation result together with the graph.

Further, in the apparatus in accordance with another embodiment of the present invention, in the step (c), the processor is further configured to output a degree of agreement between a graph obtained by connecting the standard values and a graph obtained by connecting the average standard values of the control group together with the graph, for the divided regions.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF THE PREFERRED EMBODIMENTS

Hereinafter, preferred embodiments of the present invention will be described with reference to the drawings.

Here, the above-mentioned objects, features and advantages of the present invention will become more apparent through the following detailed description in conjunction with the accompanying drawings. However, it is to be understood that the present invention may be variously modified and embodied, and thus particular embodiments thereof will be illustrated in the drawings and described in detail.

Like reference numerals throughout the specification refer to like elements in principle. In addition, components having the same function within the scope of the same idea shown in the drawings of each embodiment will be described using the same reference numerals.

When a part "includes" an element, in the entire specification herein, unless described to the contrary, the term "includes" does not indicate that another element is excluded but instead indicates that the other element may be further included. In addition, the terms including "unit" and "module" described in the specification refer to units of performing at least one function or operation, which may be implemented by hardware or software, or by a combination of hardware and software.

When it is determined that the detailed description of the known technology or configuration related to the present invention may unnecessarily obscure the subject matter of the present invention, the detailed description thereof will be omitted. In addition, numbers (e.g., first, second, and the like) used in the description of the present specification are only identification symbols for distinguishing one component from other components.

Figure 1:
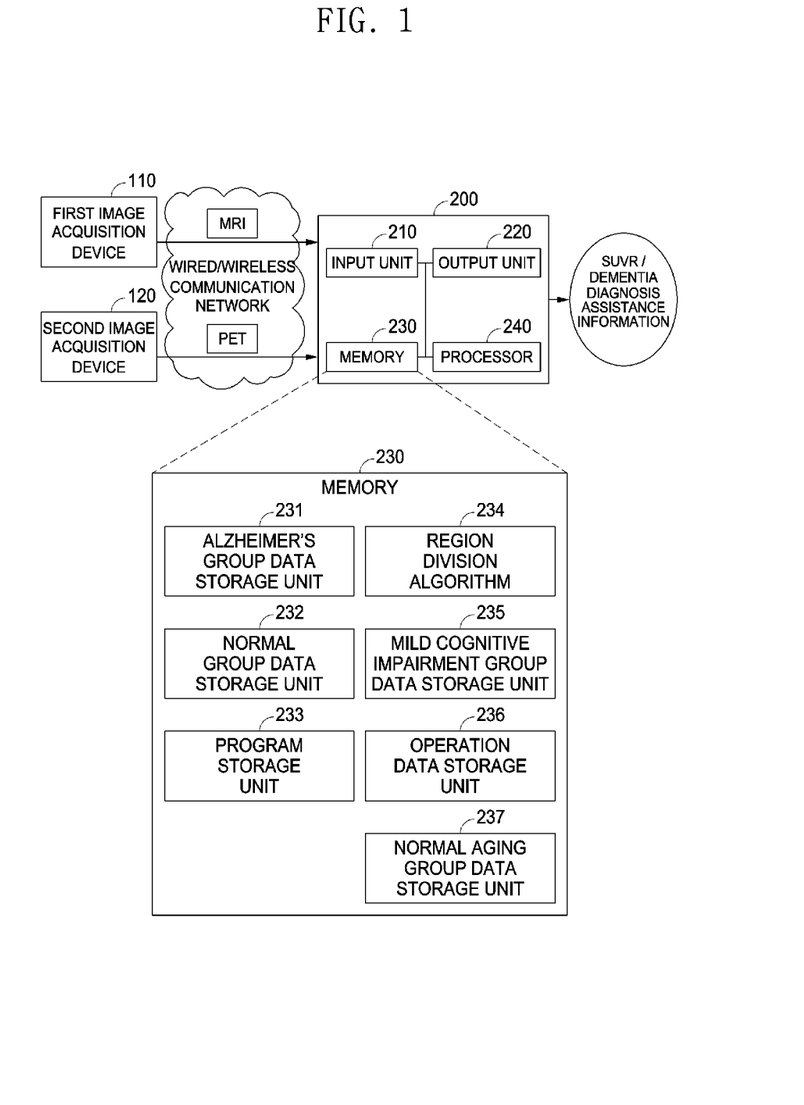
FIG. 1 is a diagram illustrating an apparatus for providing dementia diagnosis assistance information in accordance with a preferred embodiment of the present invention.

FIG. 1 is a diagram illustrating an apparatus 200 for providing dementia diagnosis assistance information in accordance with a preferred embodiment of the present invention.

Referring to FIG. 1, the apparatus 200 for providing dementia diagnosis assistance information in accordance with an embodiment of the present invention is connected to a first image acquisition device 110 and a second image acquisition device 120 through a wired or wireless communication network, and receives an MRI image and a PET image from the first image acquisition device 110 and the second image acquisition device 120, respectively.

Here, the wired or wireless communication network may be implemented as any one of a mobile phone mobile communication network, a local area network (LAN), a wireless personal area network (WPAN), and a wireless local area network (WLAN), or may be implemented as a combination of two or more of them.

In a preferred embodiment of the present invention, the first image acquisition device 110 may be implemented as an MRI imaging device that outputs an MRI brain image by imaging a brain region of a subject for diagnosis, the second image acquisition device 120 may be implemented as a PET imaging device that outputs a PET brain image by imaging the brain region of a subject for diagnosis, and the apparatus 200 for providing dementia diagnosis assistance information may receive the MRI brain image and the PET brain image in real time at the same time as imaging.

In addition, the first image acquisition device 110 and the second image acquisition device 120 may capture the MRI brain image and the PET brain image and store the images therein, and when the apparatus 200 for providing dementia diagnosis assistance information requests the MRI brain image and PET brain image of the subject for diagnosis, the first image acquisition device 110 and the second image acquisition device 120 may provide the MRI brain image and PET brain image of the subject for diagnosis to the apparatus 200 for providing dementia diagnosis assistance information.

In addition, the first image acquisition device 110 and the second image acquisition device 120 may be implemented as a database server that stores MRI brain images and PET brain images of a plurality of subjects for diagnosis that have been generated in advance.

Here, the MRI brain image is preferably a T1 weighted MRI image, but is not limited thereto, and the PET brain image may be an amyloid PET image or a Tau PET image.

In addition, the apparatus 200 for providing dementia diagnosis assistance information in accordance with a preferred embodiment of the present invention includes a processor 240, a memory 230, an input unit 210, and an output unit 220.

Meanwhile, the memory 230 in accordance with a preferred embodiment of the present invention may store instructions executable by the processor 240 and programs executed by the processor 240, and store input/output data. Examples of the memory 230 include a hard disk drive (HDD), a solid state drive (SSD), a flash memory, a read-only memory (ROM), a random access memory (RAM), and the like. The memory 230 may be replaced by operating a web storage or a cloud server performing a function of a storage medium on the Internet.

When the memory 230 of the present invention is conceptually partitioned according to the data stored therein, the memory 230 includes a program storage unit 233, an Alzheimer's group data storage unit 231, and a normal group data storage unit 232, a region division algorithm 234, a mild cognitive impairment group data storage unit 235, an operation data storage unit 236, and a normal aging group data storage unit 237.

The program storage unit 233 stores a program including instructions for being loaded into the processor 240 and performing a method for providing dementia diagnosis assistance information, which will be described later with reference to FIG. 3.

The Alzheimer's group data storage unit 231 may store a registered image obtained by registering MRI brain images and PET brain images of members of the Alzheimer's group prepared in advance, and may store images obtained by dividing the registered image into a predefined number of regions and SUVR data generated for each of the divided regions. In addition, the Alzheimer's group data storage unit 231 may calculate the average value of the SUVRs of the corresponding region of all members of the group of the Alzheimer's patients for each of the divided brain regions and store the average value.

Figure 2:
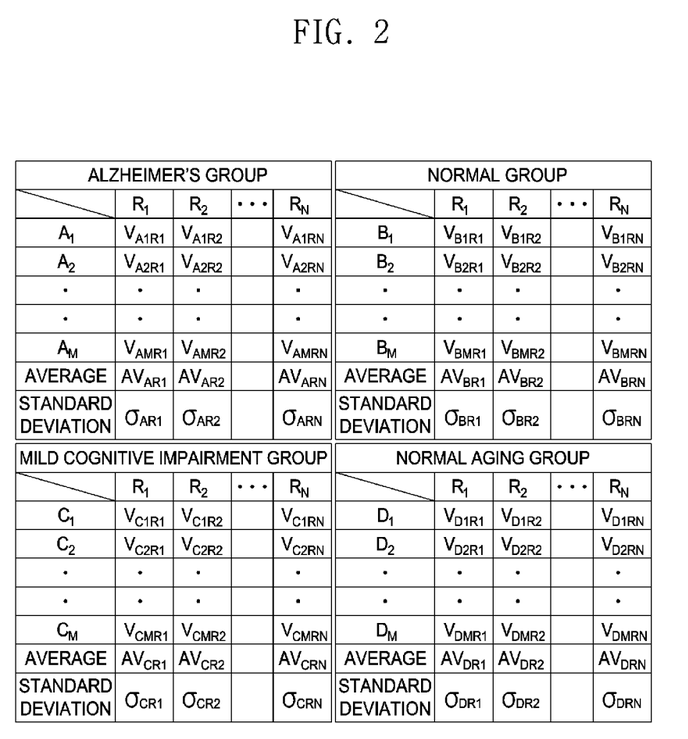
FIG. 2 is a table showing an example of Alzheimer's group data, normal group data, normal aging group data, and mild cognitive impairment group data that are stored in a memory of the present invention.

FIG. 2 is a table showing an example of Alzheimer's group data, normal group data, normal aging group data, and mild cognitive impairment group data that are stored in a memory of the present invention.

As shown in FIG. 2, data for M members $A_1$ to $A_M$ are stored in the Alzheimer's group, and for each member, N SUVR values $V_{A1R1}$ to $V_{A1RN}$, ..., $V_{AMR1}$ to $V_{AMRN}$ for N regions $R_1$ to $R_N$ obtained by dividing a brain image region of the member are stored. In addition, for each region, average values $\Delta V_{AR1}$ to $\Delta V_{ARN}$ and standard deviations $\sigma_{AR1}$ to $\sigma_{ARN}$ of the SUVRs of the corresponding region for the respective members are stored. Accordingly, the Alzheimer's group data storage unit 231 stores N average values $\Delta V_{AR1}$ to $\Delta V_{ARN}$ and standard deviations $\sigma_{AR1}$ to $\sigma_{ARN}$ of the SUVRs for each of N regions corresponding to the number of divided regions.

In a preferred embodiment of the present invention, the brain image region is divided into 97 regions according to a predefined brain map and the Alzheimer's group data storage unit 231 stores the average values and standard deviations of the SUVRs of each of the 97 regions; however, the number of regions is not limited to 97.

In addition, since only the average values and standard deviations of the SUVRs for each region are used in the process of providing dementia diagnosis assistance information in accordance with the present invention, the Alzheimer's group data storage unit 231 may store only average values $\Delta V_{AR1}$ to $\Delta V_{ARN}$ and standard deviations $\sigma_{AR1}$ to $\sigma_{ARN}$ of a predefined number of divided regions without storing the brain images of Alzheimer's members.

On the other hand, the normal group data storage unit 232 may use the same method as the Alzheimer's group data, as shown in FIG. 2 to store a registered image obtained by registering MRI brain images and PET brain images of members of the normal group and an image obtained by dividing the registered image into a predefined number of regions. In addition, the normal group data storage unit 232 may store SUVR values $V_{B1R1}$ to $V_{B1RN}$, ..., $V_{BMR1}$ to $V_{BMRN}$ calculated for each of the divided regions $R_1$ to $R_N$ of all normal members $B_1$ to $B_M$, and may store average values $\Delta V_{BR1}$ to $\Delta V_{BRN}$ and standard deviations $\sigma_{BR1}$ to $\sigma_{BRN}$ of the SUVRs of the corresponding region of all members of the normal group for each divided brain region.

In a preferred embodiment of the present invention, as with the Alzheimer's group, for the normal group, the brain image region is divided into 97 regions according to a predefined brain map and the average values and standard deviations of the SUVRs of each of the 97 regions are stored; however, the number of divided regions is not limited to 97. In addition, the normal group data storage unit 232 may store only the average values $\Delta V_{BR1}$ to $\Delta V_{BRN}$ and standard deviations $\sigma_{BR1}$ to $\sigma_{BRN}$ of the SUVRs of a predefined number of divided regions without storing brain images of normal members.

Similarly, the mild cognitive impairment group data storage unit 235 may use the same method as the normal group data, as shown in FIG. 2, to store a registered image obtained by registering MRI brain images and PET brain images of members of the mild cognitive impairment group and an image obtained by dividing the registered images into a predefined number of regions. In addition, the mild cognitive impairment group data storage unit 235 may store SUVR values $V_{C1R1}$ to $V_{C1RN}$, . . . , $V_{CMR1}$ to $V_{CMRN}$ calculated for each of the divided regions $R_1$ to $R_N$ of all mild cognitive impairment members $C_1$ to $C_M$, and may store average values $\Delta V_{CR1}$ to $\Delta V_{CRN}$ and standard deviations $\sigma_{CR1}$ to $\sigma_{CRN}$ of the SUVRs of the corresponding region of all members of the mild cognitive impairment group for each of the divided brain regions.

In a preferred embodiment of the present invention, as with the Alzheimer's group and the normal group, for the mild cognitive impairment group, the brain image region is divided into 97 regions according to a predefined brain map and the average values and the standard deviations of the SUVRs of each of the 97 regions are stored; however, the number of divided regions is not limited to 97. In addition, the mild cognitive impairment group data storage unit 235 may store only the average values $\Delta V_{CR1}$ to $\Delta V_{CRN}$ and standard deviations $\sigma_{CR1}$ to $\sigma_{CRN}$ of the SUVRs of a predefined number of divided regions without storing brain images of the mild cognitive impairment members.

Similarly, the normal aging group data storage unit 237 stores data for the elderly who have been determined to be normal among the elderly in a predefined age range. The normal aging group data storage unit 237 may use the same method as the normal group data, as shown in FIG. 2, to store a registered image obtained by registering MRI brain images and PET brain images of members of the normal aging group and an image obtained by dividing the registered images into a predefined number of regions.

In addition, the normal aging group data storage unit 237 may store SUVR values $V_{D1R1}$ to $V_{D1RN}$, . . . , $V_{DMR1}$ to $V_{DMRN}$ calculated for each of the divided regions $R_1$ to $R_N$ of all normal aging group members $D_1$ to $D_M$, and may store average values $\Delta V_{DR1}$ to $\Delta V_{DRN}$ and standard deviations $\sigma_{DR1}$ to $\sigma_{DRN}$ of the SUVRs of the corresponding region of all members of the normal aging group for each of the divided brain regions.

In a preferred embodiment of the present invention, as with the Alzheimer's group, the normal group, and the mild cognitive impairment group, for the normal aging group, the brain image region is divided into 97 regions according to a predefined brain map and the average values and the standard deviations of the SUVRs of each of the 97 regions are stored; however, the number of divided regions is not limited to 97. In addition, the normal aging group data storage unit 237 may store only the average values $\Delta V_{DR1}$ to $\Delta V_{DRN}$ and the standard deviations $\sigma_{DR1}$ to $\sigma_{DR4}$ of the SUVRs of a predefined number of divided regions without storing brain images of normal aging group members.

The region division algorithm 234 is trained by a deep learning method and stored as an algorithm trained to divide an MRI brain image into a predefined number of divided regions.

Meanwhile, the input unit 210 of the apparatus 200 for providing dementia diagnosis assistance information may be implemented as a typical input means such as a mouse and a keyboard, and may receive setting information, selection information, or the like, from the user and output received information to the processor 240. In addition, the input unit 210 may include a communication module (not shown) therein to receive MRI brain images and PET brain images from the first image acquisition device 110 and the second image acquisition device 120 through a wired/wireless communication network.

The output unit 220 may be implemented as a typical output means such as a monitor and a printer to display the data and dementia diagnosis assistance information generated by the processor 240 to the user.

The processor 240 in accordance with a preferred embodiment of the present invention may be implemented as a central processing unit (CPU) or a similar device, and performs each step of the method for providing dementia diagnosis assistance information, which will be described later with reference to FIG. 3, by executing instructions stored in the memory 230.

Figure 3:
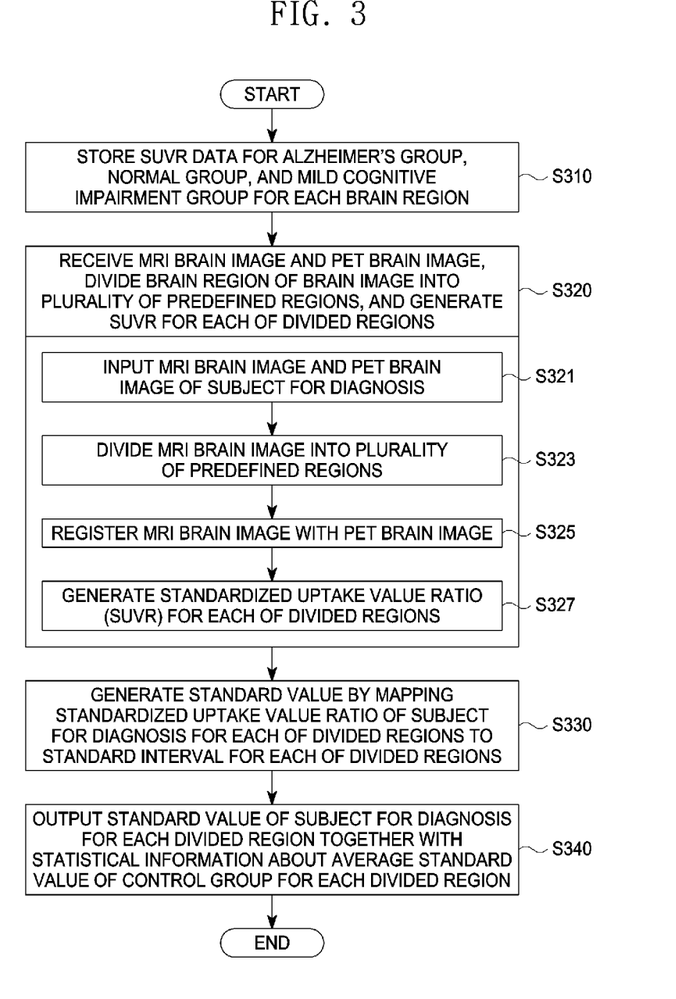
FIG. 3 is a flowchart illustrating a method for providing dementia diagnosis assistance information in accordance with a preferred embodiment of the present invention.

FIG. 3 is a flowchart illustrating a method for providing dementia diagnosis assistance information in accordance with a preferred embodiment of the present invention. With further reference to FIG. 3, a processing operation of the processor 240 of the present invention and a method for providing dementia diagnosis assistance information performed by the processor 240 in accordance with a preferred embodiment of the present invention will be described.

First, as described above, SUVR data for each of the brain regions of the Alzheimer's group, the normal group, and the mild cognitive impairment group are stored in the memory 230 of the present invention (S310). An example of SUVR data for each of the brain regions of the Alzheimer's group, the normal group, and the mild cognitive impairment group stored in the memory 230 is as described above with reference to FIG. 2. A detailed configuration of the step S310 will be described later with reference to FIG. 9.

Then, the processor 240 of the apparatus 200 for providing dementia diagnosis assistance information receives an MRI brain image and a PET brain image of a subject for diagnosis with dementia, divides the brain region of the brain image into a plurality of predefined regions, and generates the SUVR for each divided region (S320).

Figure 4:
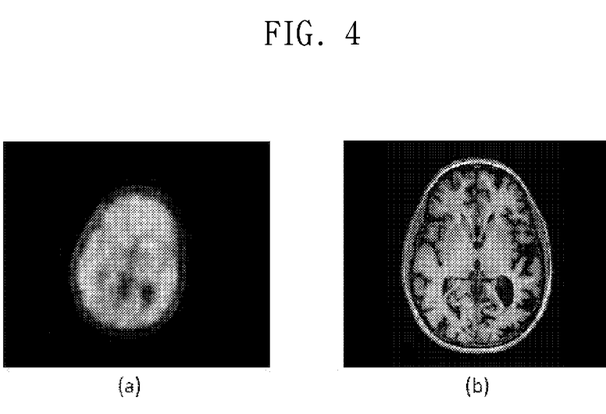
FIG. 4 is a diagram illustrating an example of an MRI brain image and a PET brain image that are input to an apparatus for providing dementia diagnosis assistance information.

Describing step S320 in more detail, as shown in (a) and (b) of FIG. 4, the processor 240 receives the MRI brain image of the subject for diagnosis from the first image acquisition device 110, and receives the PET brain image of the subject for diagnosis from the second image acquisition device 120 (S321). In this case, the MRI brain image is preferably a T1-weighted MRI brain image, and the PET brain image may be an amyloid PET image or a tau PET image as needed.

The processor 240 divides the MRI brain image into a plurality of predefined regions (refer to FIG. 5) by using a deep learning-based region division algorithm stored in the memory 230 (S323). As described above, in the preferred embodiment of the present invention, the processor 240 divides the MRI brain image into 97 regions of interest according to the brain map; however, the division method and the number of divided regions are not limited thereto.

Figure 6:
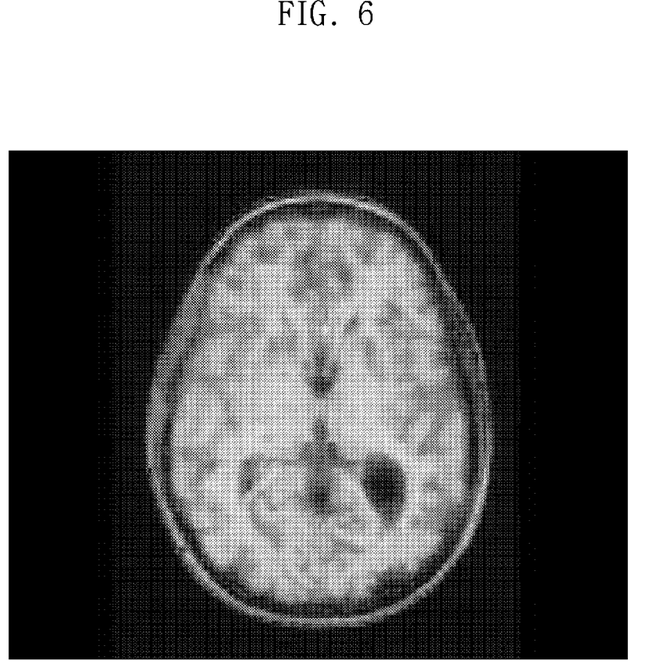
FIG. 6 is a diagram illustrating an example of a registered image in accordance with a preferred embodiment of the present invention.

Then, the processor 240 performs image registration on the MRI brain image and the PET brain image so that the two images are located in the same space through rigid transform (S325). FIG. 6 illustrates an example of an image in which an MRI brain image and a PET brain image are matched. As shown in FIG. 6, in the registered image, the processor 240 may identify regions corresponding to the divided regions in the PET brain image through the divided regions of the MRI brain image.

The processor 240 generates a standardized uptake value ratio (SUVR) for each divided region (S327).

The standardized uptake value ratio (SUVR) represents a ratio of amyloid (or tau) standardized uptake value (SUV) from two different regions (target and reference region) within the same amyloid (or tau) PET image, and the amyloid (or tau) standardized uptake value (SUV) may represent the ratio of the concentration of radioactivity of the image to the concentration of radioactivity of the whole injected body. The method for obtaining the standardized uptake value ratio (SUVR) is a known technique in the technical field of the present invention, and thus a detailed description thereof will be omitted.

When the standardized uptake value ratio (SUVR) of the subject for diagnosis is obtained for each of the divided regions $R_1$ to $R_N$ in step S327, the respective standardized uptake value ratios $V_{SR1}$ to $V_{SRN}$ for the divided regions $R_1$ to $R_N$ are stored in the memory 230.

Next, the processor 240 generates a standard value by mapping the standardized uptake value ratio $V_{SR1}$ to $V_{SRN}$ of the subject for diagnosis for each of the divided regions to a standard interval for each of the divided regions (S330).

Here, the standard value represents a degree of proximity of the standardized uptake value ratio of the subject for diagnosis for each of divided regions to an average value of standardized uptake value ratios of a group of Alzheimer's patients and an average value of standardized uptake value ratios of a normal group.

In addition, the standard interval to which the standardized uptake value ratio of the subject for diagnosis for each of the divided regions is to be mapped is defined by setting, as both ends of a regular interval, the average value of the standardized uptake value ratios of the group of the Alzheimer's patients and the average value of the standardized uptake value ratios of the normal group for each of the plurality of divided regions.

In the preferred embodiment of the present invention, the standard interval is an interval generated by transforming the average value of the standardized uptake value ratios of the group of the Alzheimer's patients to correspond to 100 according to a predetermined transformation formula and transforming the average value of the standardized uptake value ratios of the normal group to correspond to 0 according to the transformation formula, and the standard value of the standardized uptake value ratio of the subject for diagnosis for each of the regions is a value obtained by transforming the standardized uptake value ratio according to the same transformation formula. In this case, the transformation formula may be defined as in Equation 1 below.

$$y = \frac{(x-B)}{(A-B)} \times 100 \quad \text{[Equation 1]}$$

In the Equation 1, A represents the average value of the standardized uptake value ratios of the group of the Alzheimer's patients, B represents the average value of the standardized uptake value ratios of the normal group, and x represents the SUVR of the subject for diagnosis, which is a parameter to be transformed.

Figure 7:
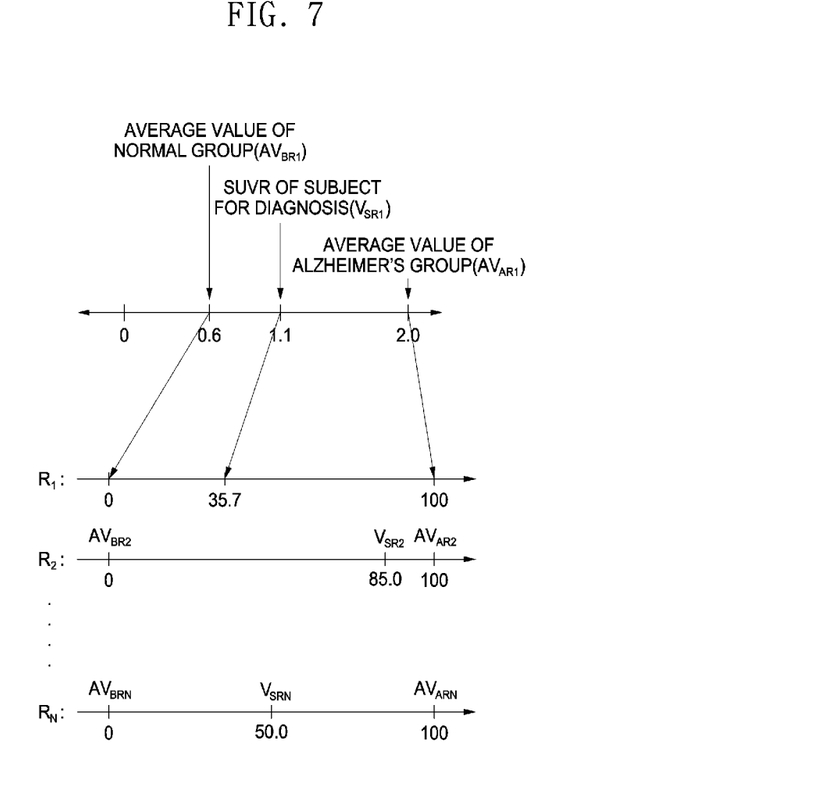
FIG. 7 is a diagram for describing a standard interval obtained from average values of standardized uptake value ratios of a group of Alzheimer's patients and a normal group for each region in accordance with a preferred embodiment of the present invention, and a standard value of a subject for diagnosis mapped for each region accordingly.

FIG. 7 is a diagram for describing a standard interval obtained from average values of standardized uptake value ratios of a group of Alzheimer's patients and a normal group for each region in accordance with a preferred embodiment of the present invention, and a standard value of a subject for diagnosis mapped for each region accordingly.

Referring to FIG. 7, assuming that the average value $\Delta V_{AR1}$ of the group of Alzheimer's patients in a first divided region $R_1$ is 2.0, the average value $\Delta V_{BR1}$ of the normal group is 0.6, and the SUVR of the subject for diagnosis is 1.1, in the standard interval of the divided region $R_1$, the average value $\Delta V_{BR1}$ of the normal group of 0.6 corresponds to 0, the average value $\Delta V_{AR1}$ of the group of Alzheimer's patients of 2.0 corresponds to 100, and the SUVR of the subject for diagnosis of 1.1 corresponds to 35.7 according to Equation 1 above.

In the above example, assuming that a reference value for determining whether PET is positive and negative is 1.1, the SUVR of the divided region $R_1$ of the subject for diagnosis is 1.1, which is at a borderline for determining whether PET is positive and negative, but when transformed to a standard interval, the standard value does not exceed 50, which is closer to the normal group, which makes it possible to provide useful information in determining whether PET is positive and negative.

In the same manner, for each of the remaining divided regions $R_2$ to $R_N$, the processor 240 generates a standard interval by transforming the average value of the normal group to 0 and transforming the average value of the group of Alzheimer's patients to 100, and generates a standard value to be mapped to the standard interval by transforming the SUVR of the subject for diagnosis of dementia in the same way.

In the above example, the standard interval was set to 0 to 100, but according to another embodiment, by modifying Equation 1 above to transform the average value of the SUVRs of the Alzheimer's group to 1, the standard interval may be set to 0 to 1.

Meanwhile, when the standard value of the standardized uptake value ratios of the subject for diagnosis is generated for each of the divided regions, the processor 240 outputs the standard value of each divided region of the subject for diagnosis as the dementia diagnosis assistance information, together with statistical information about the average standard value of the control group for each divided region (S340).

Here, the control group may include the group of Alzheimer's patients, the normal group, the normal aging group, and the mild cognitive impairment group stored in the memory 230. In addition, the statistical information about the average standard value of the control group may include a standard value obtained by transforming the average value of the control group for the corresponding divided region according to Equation 1 above and a standard deviation corresponding thereto.

Figure 8:
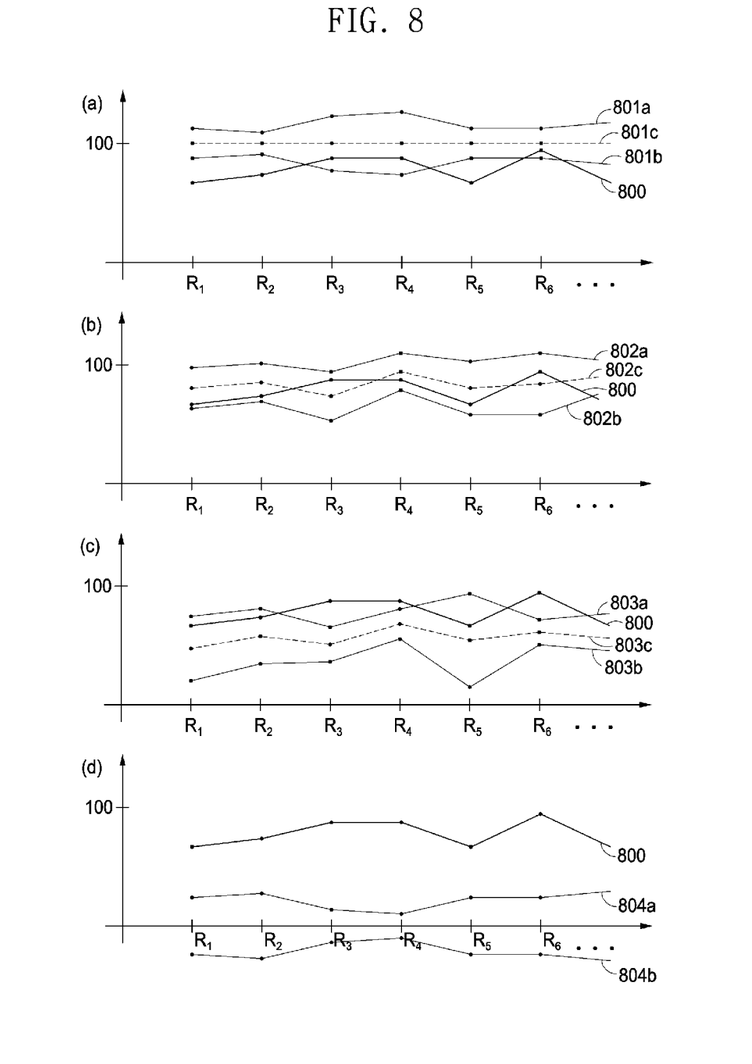
FIG. 8 is a diagram illustrating an example of dementia diagnosis assistance information output in accordance with a preferred embodiment of the present invention.

FIG. 8 is a diagram illustrating an example of dementia diagnosis assistance information output in step S340 in accordance with a preferred embodiment of the present invention.

Describing a more specific example with reference to FIG. 8, as shown in FIG. 8, the processor 240 may output a pair of values greater by a predefined value and less by the predefined value, than the average standard value of the control group, together with the standard value of the subject for diagnosis of dementia as a graph, where the predefined value may be a standard deviation. For reference, in the example shown in FIG. 8, only six divided regions are indicated for convenience of description.

In the example shown in FIG. 8, (a) shows the average standard value and standard deviation for each of the divided regions of the Alzheimer's group, and also shows the standard value for each of the divided regions of the subject for diagnosis of dementia. In (a) of FIG. 8, standard values (average standard values) of the average values of the Alzheimer's group are located on a horizontal line 801c having a constant value of 100 according to Equation 1 above, and when the values are connected, a horizontal line having a value of 100 is obtained. At this time, there is a difference in the standard deviations for the regions, and thus they are arranged to correspond to each other around 100, and when the values obtained for each of the divided regions are connected, two graphs 801a and 801b of standard deviations are drawn.

Here, when points are drawn to correspond to the SUVR standard values of the subject for diagnosis of dementia for each of the divided regions and the points are connected to each other, a line graph 800 is displayed together.

When the graph of the SUVR standard values of the subject for diagnosis of dementia is located inside graphs 801a and 801b of the standard deviations of the group of Alzheimer's patients in all divided regions, it is possible to determine that the subject for diagnosis of dementia is highly likely to have dementia since the SUVR characteristic of the subject for diagnosis of dementia shows the same pattern as the Alzheimer's patients, and to output, to the subject for diagnosis of dementia, a diagnosis result of Alzheimer's dementia.

However, when the graph of the SUVR standard values of the subject for diagnosis of dementia is located inside the graphs 801a and 801b of the standard deviations of the group of Alzheimer's patients only in some divided regions, it is possible to determine that the subject for diagnosis of dementia has a low likeliness of Alzheimer's dementia since the SUVR characteristic of the subject for diagnosis does not show the same pattern as the Alzheimer's patients. Accordingly, it is possible to output a diagnosis result indicating that the subject for diagnosis of dementia does not have Alzheimer's dementia, but may have dementia caused by other factors such as vascular dementia or Lewy body dementia.

In the same manner, the processor 240 displays, for each divided region, the average standard values calculated by transforming the average values of the mild cognitive impairment group for each divided region according to Equation 1 above, or the average standard values calculated in advance and stored in the memory 230, and displays a line graph 802c obtained by connecting the average standard values.

In addition, the processor 240 displays standard deviations centered on the average standard values of the mild cognitive impairment group for each of the divided regions, and displays graphs 802a and 802b of the standard deviations by connecting the standard deviations to each other. In addition, in the same manner as shown in (a) of FIG. 8, the processor 240 draws points corresponding to the SUVR standard values of the subject for diagnosis of dementia for each of the divided regions, and displays a line graph 800 obtained by connecting the points to each other together.

Referring to (b) of FIG. 8, the graph 800 of the SUVR standard values of the subject for diagnosis of dementia is included in the graphs 802a and 802b of the standard deviations of the mild cognitive impairment group, and thus it can be seen that the subject for diagnosis of dementia shows the same pattern as the mild cognitive impairment group. Accordingly, a diagnosis result indicating that the subject for diagnosis has mild cognitive impairment may be output.

In the same manner, as shown in (c) of FIG. 8, the processor 240 transforms the average values of the normal aging group for each of the divided regions according to Equation 1 above, and displays a graph obtained by connecting the transformed values to each other. In addition, the processor 240 displays graphs 803a and 803b of the standard deviations obtained by connecting the standard deviations of the normal aging group together.

In addition, in the same manner as shown in (a) of FIG. 8, the processor 240 draws points corresponding to the SUVR standard values of the subject for diagnosis of dementia for each of the divided regions, and displays the line graph 800 obtained by connecting the points to each other together.

Referring to (c) of FIG. 8, the graph 800 of the SUVR standard value of the subject for diagnosis of dementia is only partially included in graphs 803c and 803b of the standard deviations of the normal aging group, and thus it can be seen that the subject for diagnosis of dementia does not belong to the normal aging group.

Finally, as shown in (d) of FIG. 8, the processor 240 transforms the average values of the normal group for each of the divided regions according to Equation 1 above, and displays a graph obtained by connecting the transformed values to each other. In addition, the processor 240 displays graphs 804a and 804b of the standard deviations obtained by connecting the standard deviations of the normal group together.

Since the standard value obtained by transforming the average value of the normal group for each of the divided regions according to Equation 1 is 0, graphs 804a and 804b of the standard deviations of the normal group are displayed as a pair arranged to face each other with respect to a horizontal line passing through the origin. In addition, the processor 240 draws points corresponding to the SUVR standard values of the subject for diagnosis of dementia for each of divided regions and displays the line graph 800 obtained by connecting the points to each other together.

As shown in (d) of FIG. 8, the graph 800 of the SUVR standard values of the subject for diagnosis of dementia does not have a region included between the graphs 804a and 804b of the standard deviations of the normal group, and thus it can be seen that the subject for diagnosis of dementia shows a significantly different pattern from the normal group.

Meanwhile, the processor 240 may calculate a proportion of divided regions where the standard value of the subject for diagnosis of dementia for each divided region is located between a pair of values (standard deviations) of the control group or a proportion of divided regions where the standard value for each divided region is located outside the pair of values (standard deviations) of the control group, and may display the calculated proportion as statistical information together with the graphs.

For example, when the number of divided regions reaches 97, it is difficult to determine the number of divided regions for which the standard values of the subject for diagnosis of dementia are included between the graphs of the standard deviations by using only the graphs. Accordingly, the processor 240 may count the number of divided regions for which the standard values are included between the graphs of the standard deviations among all the divided regions, and display the proportion of the counted divided regions in the total divided regions together with a graph.

In (a) of FIG. 8, among the 6 divided regions displayed, there are three divided regions for which the standard values are included between the graphs 801a and 801b of the standard deviations, so "proportion of the regions included between the graphs of the standard deviations: 1/2" may be displayed together with a graph.

Similarly, in (b) of FIG. 8, for all of the six divided regions displayed, the standard values are included between the graphs 802a and 802b of the standard deviations, so "proportion of the regions included between the graphs of the standard deviations: 1/1" may be displayed together with a graph.

In addition, the processor 240 may set a threshold value for the proportion of the regions for which the SUVR standard values of the subject for diagnosis of dementia are included between the graphs of the standard deviations, estimate that the subject for diagnosis of dementia belongs to the control group when the proportion is greater than or equal to the threshold value, and output an estimation result together with a graph. For example, assuming that the threshold value is set to 90%, the proportion of the standard values of the subject for diagnosis of dementia included between the graphs 802a and 802b of the standard deviations of the mild cognitive impairment group exceeds the threshold value of 90%, and thus, the processor 240 may output that the subject for diagnosis of dementia has mild cognitive impairment with a graph.

In addition, the processor 240 may also output a degree of agreement between the graph obtained by connecting the SUVR standard values of the subject for diagnosis of dementia and the graph obtained by connecting the average standard values of the control group, for the divided regions. For example, the closer the sum of the absolute values obtained by subtracting the average standard values of the control group from the SUVR standard values of the subject for diagnosis of dementia to 0, the higher the degree of agreement between the graphs. Therefore, the processor 240 may calculate |the SUVR standard value of the subject for diagnosis of dementia–the average standard value of the control group| for all the divided regions, and may calculate the degree of agreement by using the sum of the values for all the divided regions and display it together.

Figure 9:
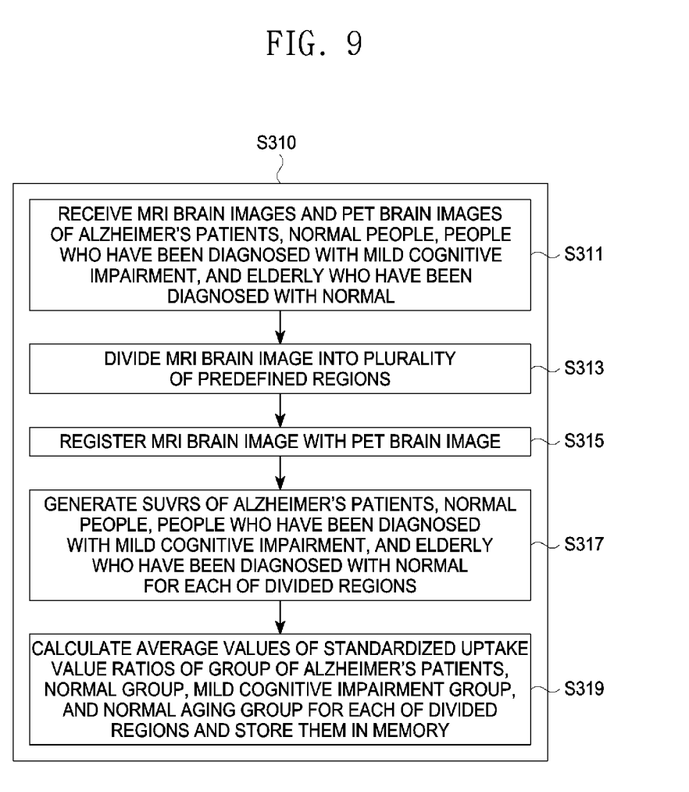
FIG. 9 is a flowchart for describing a process of obtaining average values of the SUVRs of an Alzheimer's group, a normal group, a mild cognitive impairment group, and a normal aging group for each divided region and storing the average values of the SUVRs in a memory in accordance with a preferred embodiment of the present invention.

FIG. 9 is a flowchart for describing a process of obtaining average values of the SUVRs of the Alzheimer's group, the normal group, the mild cognitive impairment group, and the normal aging group for each divided region and storing the average values of the SUVRs in the memory 230, in step S310 shown in FIG. 3, in accordance with a preferred embodiment of the present invention.

The process of calculating the average values of the SUVRs of the Alzheimer's group, the normal group, the mild cognitive impairment group, and the normal aging group for each of the divided regions is the same as the above-described step S320, except that the subjects are members of the group of Alzheimer's patients, members of the normal group, members of the mild cognitive impairment group, and members of the normal aging group.

Accordingly, briefly describing only the overall flow with reference to FIG. 9, the processor 240 receives MRI brain images of Alzheimer's patients, normal people, people who have been diagnosed with mild cognitive impairment, and the elderly who have been diagnosed with normal from the first image acquisition device 110, and receives PET brain images of Alzheimer's patients, the normal people, the people who have been diagnosed with mild cognitive impairment, and the elderly who have been diagnosed with normal from the second image acquisition device 120 (S311). In this case, the MRI brain image is preferably a T1-weighted MRI brain image, and the PET brain image may be an amyloid PET image or a tau PET image as needed.

Figure 5:
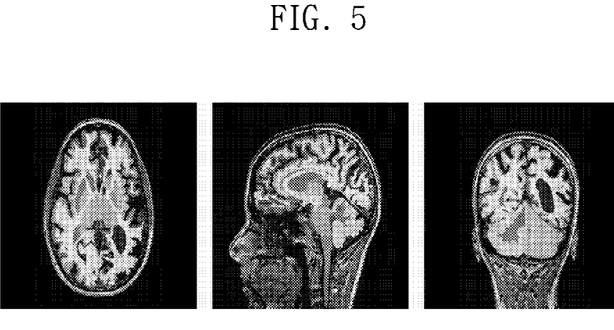
FIG. 5 is a diagram illustrating an example of divided regions of a brain image in accordance with a preferred embodiment of the present invention.

As shown in FIG. 5, the processor 240 divides the MRI brain image into a plurality of predefined regions by using a deep learning-based region division algorithm stored in the memory 230 (S313). As described above, in the preferred embodiment of the present invention, the processor 240 divides the MRI brain image into 97 regions of interest according to the brain map; however, the division method and the number of divided regions are not limited thereto.

Then, the processor 240 performs image registration on the MRI brain image and the PET brain image so that the two images are located in the same space through rigid transform (S315).

The processor 240 generates standardized uptake value ratios (SUVR) of the Alzheimer's patients, the normal people, the people who have been diagnosed with mild cognitive impairment, and the elderly who have been diagnosed with normal for each divided region and store them as shown in FIG. 2 (S317).

Then, the processor 240 calculates the average values $\Delta V_{AR1}$ to $\Delta V_{ARN}$, $\Delta V_{BR1}$ to $\Delta V_{BRN}$, $\Delta V_{CR1}$ to $\Delta V_{CRN}$, and $\Delta V_{DR1}$ to $\Delta V_{DRN}$ and the standard deviations $\sigma_{AR1}$ to $\sigma_{ARN}$, $\sigma_{BR1}$ to $\sigma_{BRN}$, $\sigma_{CR1}$ to $\sigma_{CRN}$, $\sigma_{DR1}$ to $\sigma_{DRN}$ of the standardized uptake value ratios of the group of Alzheimer's patients, the normal group, the mild cognitive impairment group, and the normal aging group for each of the divided regions $R_1$ to $R_N$ and stores them in the memory 230 (S319).

The method for providing dementia diagnosis assistance information in accordance with a preferred embodiment of the present invention described above may be implemented as a computer program stored in a non-transitory storage medium by being implemented as computer-executable instructions.

In the apparatus and method for providing dementia diagnosis assistance information in accordance with preferred embodiments of the present invention, an MRI brain image and a PET brain image of a subject for diagnosis are received, the MRI brain image is divided into a plurality of regions, and then the MRI brain image is matched with the PET brain image. Then, a standardized uptake value ratio of each divided region is obtained from the registered image, and for each divided region, a standard value indicating the degree of proximity of a standardized uptake value ratio of the subject for diagnosis to the average value of the standardized uptake value ratios of the group of the Alzheimer's patients and the average value of the standardized uptake value ratios of the normal group, which are stored in advance, is obtained. Then, by displaying the standard value of the standardized uptake value ratio of the subject for diagnosis together with the average value and the range of the standard deviation of each control group for each of the divided regions as a graph and presenting various statistical information, it is possible to provide various information useful for dementia diagnosis and ultimately, it is possible to improve the accuracy of dementia diagnosis.

In particular, the present invention enables health care providers to select an appropriate treatment plan and treatment method by diagnosing the subject for diagnosis as Alzheimer's dementia with high probability when the standard values of the standardized uptake value ratios of the subject for diagnosis is within the range of the standard deviation of the group of Alzheimer's patients and providing the fact, and by providing information that the subject for diagnosis does not fall under Alzheimer's dementia, but may fall under other factors, such as vascular dementia or Lewy body dementia, when the standard values of the standardized uptake value ratios of the subject for diagnosis is not within the range of the standard deviation of the group of Alzheimer's patients.

The storage medium includes all kinds of recording devices in which data that may be read by a computer system is stored. Examples of computer-readable storage media include read only memory (ROM), random access memory (RAM), compact disc ROMs (CD-ROM), magnetic tapes, floppy disks, and optical data storage devices. In addition, the computer-readable storage medium may be distributed in a computer system connected through a network, so that the computer-readable code may be stored and executed in a distributed manner.

As described above, the present invention has been shown and described with reference to preferred embodiments thereof. It will be understood by those skilled in the art that various modifications in form may be made therein without departing from the spirit and scope of the invention as defined by the appended claims. Therefore, the disclosed embodiments should be considered in an illustrative sense and not for purposes of limitation. The scope of the invention is defined not by the detailed description of the invention but by the appended claims, and all differences within the scope will be construed as being included in the invention.

What is claimed is:

1. A method for providing Alzheimer's diagnosis assistance information that is performed in an apparatus coupled to one or more Magnetic Resonance Imaging (MRI) and one or more Positron Emission Tomography (PET) image acquisition devices for providing Alzheimer's diagnosis assistance information, the apparatus including a processor and a memory for storing predetermined instructions, the method comprising:

(a) obtaining an MRI brain image and a PET brain image of a living subject's brain via said one or more MRI and PET image acquisition devices, said one or more MRI and PET image acquisition devices configured to transmit said brain image to said apparatus;

(b) dividing said MRI brain image and said PET brain image into a plurality of predefined anatomical regions;

(c) registering said predefined anatomical regions of said MRI brain image with said PET brain image;

(d) calculating a standardized uptake value ratio (SUVR) for each of said predefined anatomical regions;

(e) obtaining a standard value by mapping the standardized uptake value ratio of each divided region to a standard interval defined in advance for each divided region; and (f) outputting the standard value of each divided region together with statistical information about an average standard value of a comparison group for each divided region, wherein the standard value represents a degree of proximity of the standardized uptake value ratio to an average value of standardized uptake value ratios of a group of Alzheimer's patients and an average value of standardized uptake value ratios of a normal group, wherein the standard interval is defined by setting, as both ends of a regular interval, the average value of the standardized uptake value ratios of the group of the Alzheimer's patients and the average value of the standardized uptake value ratios of the normal group for a region corresponding to each of the plurality of divided regions, wherein the standard interval is an interval generated by transforming the average value of the standardized uptake value ratios of the normal group to correspond to 0 according to a predetermined transformation formula, and transforming the average value of the standardized uptake value ratios of the group of the Alzheimer's patients to correspond to a predetermined number greater than 0 according to the transformation formula, and the standard value of the subject is obtained by transforming the standardized uptake value ratio according to the transformation formula, wherein the step (e) comprises:

outputting a pair of values as large as a predefined value and small as a predefined value from the average standard value of the comparison group together with the standard value as a graph, for each divided region, displaying a proportion of divided regions where the standard value is located between the pair of values of the comparison group or a proportion of divided regions where the standard value deviates from the pair of values of the comparison group together with the graph, and outputting a degree of agreement between a graph obtained by connecting the standard values and a graph obtained by connecting the average standard values of the comparison group together with the graph, for the divided regions.

2. The method of claim 1, wherein the transformation formula is defined as $$y = \frac{(x-B)}{(A-B)} \times 100,$$

where A represents the average value of the standardized uptake value ratios of the group of the Alzheimer's patients, B represents the average value of the standardized uptake value ratios of the normal group, and x represents a Standardized Uptake Value Ratio (SVUR) of said living subject to be transformed.

3. The method of claim 1, wherein the step (f) comprises outputting a pair of values that differ by a standard deviation from the average standard value of the comparison group together with the standard value, for each divided region.

4. A computer program that is stored in a non-transitory storage medium and executed in a computer including a processor, said non-transitory storage medium coupled to one or more Magnetic Resonance Imaging (MRI) and one or more Positron Emission Tomography (PET) image acquisition devices, the computer program causing the computer to execute:

(a) obtaining an MRI brain image and a PET brain image of a living subject's brain via said one or more MRI and PET image acquisition devices, said one or more MRI and PET image acquisition devices configured to transmit said brain image to an apparatus;

(b) dividing said MRI brain image and said PET brain image into a plurality of predefined anatomical regions;

(c) registering said predefined anatomical regions of said MRI brain image with said PET brain image;

(d) calculating a standardized uptake value ratio (SUVR) for each of said predefined anatomical regions;

(e) obtaining a standard value by mapping the standardized uptake value ratio of each divided region to a standard interval defined in advance for each divided region; and (f) outputting the standard value of each divided region together with statistical information about an average standard value of a comparison group for each divided region, wherein the standard value represents a degree of proximity of the standardized uptake value ratio to an average value of standardized uptake value ratios of a group of Alzheimer's patients and an average value of standardized uptake value ratios of a normal group, wherein the standard interval is defined by setting, as both ends of a regular interval, the average value of the standardized uptake value ratios of the group of the Alzheimer's patients and the average value of the standardized uptake value ratios of the normal group for a region corresponding to each of the plurality of divided regions, wherein the standard interval is an interval generated by transforming the average value of the standardized uptake value ratios of the normal group to correspond to 0 according to a predetermined transformation formula, and transforming the average value of the standardized uptake value ratios of the group of the Alzheimer's patients to correspond to a predetermined number greater than 0 according to the transformation formula, and the standard value of the subject is obtained by transforming the standardized uptake value ratio according to the transformation formula, wherein in the step (e), the computer program causing the computer to further execute:

outputting a pair of values as large as a predefined value and small as a predefined value from the average standard value of the comparison group together with the standard value as a graph, for each divided region, displaying a proportion of divided regions where the standard value is located between the pair of values of the comparison group or a proportion of divided regions where the standard value deviates from the pair of values of the comparison group together with the graph, and outputting a degree of agreement between a graph obtained by connecting the standard values and a graph obtained by connecting the average standard values of the comparison group together with the graph, for the divided regions.

5. A system for providing Alzheimer's diagnosis assistance information, comprising:

one or more Magnetic Resonance Imaging (MRI) and one or more Positron Emission Tomography (PET) image acquisition devices coupled to an apparatus, said one or more MRI and PET image acquisition devices configured to obtain an MRI brain image and a PET brain image of a living subject's brain and transmit said brain images to an apparatus, where in said apparatus comprises:

a processor; and a memory for storing predetermined instructions, wherein the processor is configured to, when executing the instructions stored in the memory:

(a) calculate a standardized uptake value ratio (SUVR) for each of divided regions obtained by dividing a brain region of said MRI brain image and said PET brain image for diagnosis into a plurality of predefined anatomical regions;

(b) register said predefined anatomical regions of said MRI brain image with said PET brain image (c) calculate a standardized uptake value ratio (SUVR) for each of said predefined anatomical regions;

(d) obtain a standard value by mapping the standardized uptake value ratio of each divided region to a standard interval defined in advance for each divided region; and (e) output the standard value of each divided region together with statistical information about an average standard value of a comparison group for each divided region, wherein the standard value represents a degree of proximity of the standardized uptake value ratio to an average value of standardized uptake value ratios of a group of Alzheimer's patients and an average value of standardized uptake value ratios of a normal group, wherein the standard interval is defined by setting, as both ends of a regular interval, the average value of the standardized uptake value ratios of the group of the Alzheimer's patients and the average value of the standardized uptake value ratios of the normal group for a region corresponding to each of the plurality of divided regions, wherein the standard interval is an interval generated by transforming the average value of the standardized uptake value ratios of the normal group to correspond to 0 according to a predetermined transformation formula, and transforming the average value of the standardized uptake value ratios of the group of the Alzheimer's patients to correspond to a predetermined number greater than 0 according to the transformation formula, and the standard value of the subject is obtained by transforming the standardized uptake value ratio according to the transformation formula, wherein in the step (e), the processor is further configured to output a pair of values as large as a predefined value and small as a predefined value from the average standard value of the comparison group together with the standard value as a graph, for each divided region, display a proportion of divided regions where the standard value is located between the pair of values of the comparison group or a proportion of divided regions where the standard value deviates from the pair of values of the comparison group together with the graph, and output a degree of agreement between a graph obtained by connecting the standard values and a graph obtained by connecting the average standard values of the comparison group together with the graph, for the divided regions.

6. The apparatus of claim 5, wherein in the step (e), the processor is further configured to output a pair of values that differ by a standard deviation from the average standard value of the comparison group together with the standard value, for each divided region.

* * * * *